Figure 1:
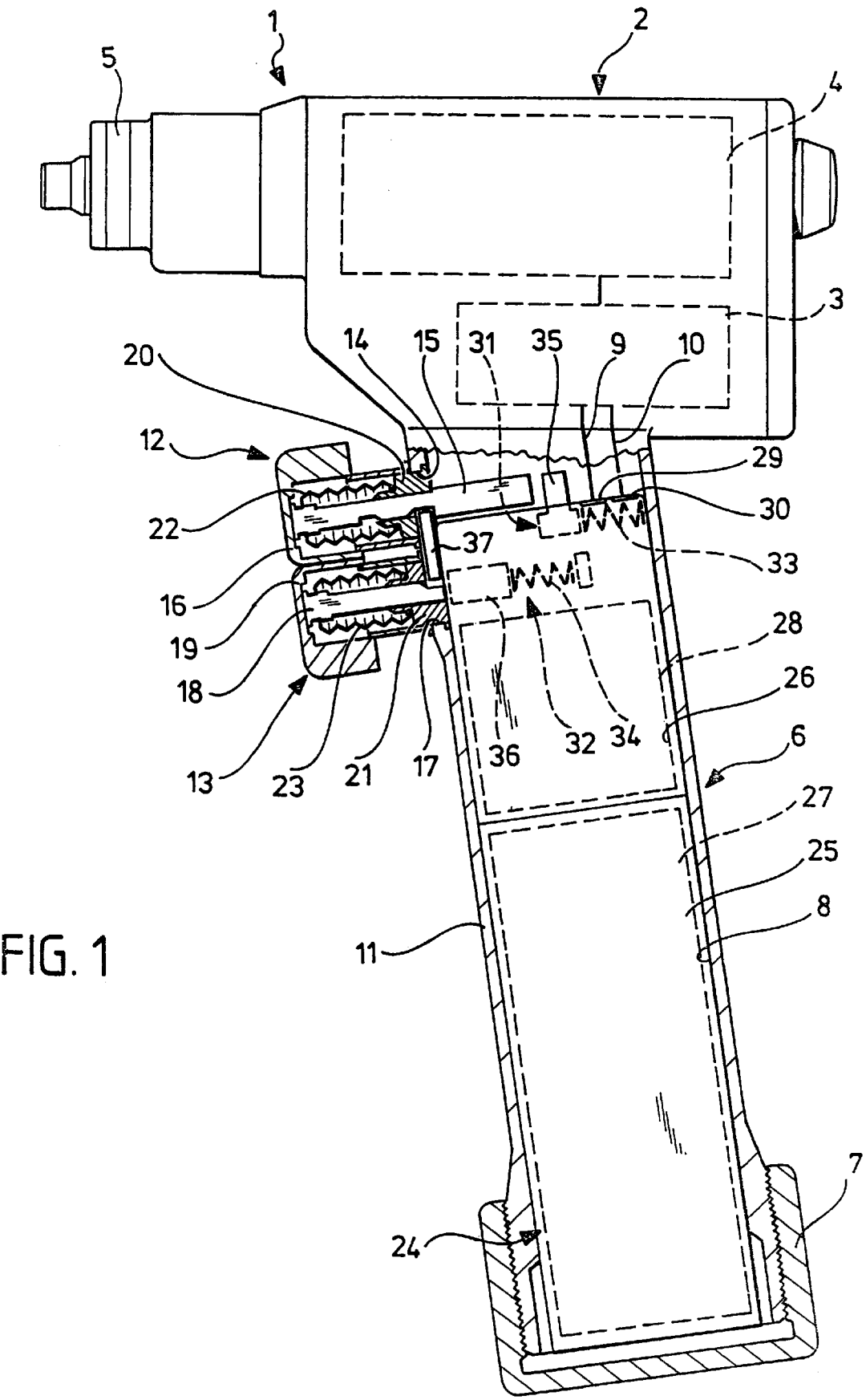

United States Patent [19]
Hoegerle

[11] Patent Number: 6,059,806
[45] Date of Patent: May 9, 2000

[54] DRILL FOR SURGICAL PURPOSES

[75] Inventor: Roland Alois Hoegerle, Tuttlingen, Germany

[73] Assignee: Aesculap A.G. & Co. K.G., Tuttlingen, Germany

[21] Appl. No.: 09/128,926

[22] Filed: Aug. 5, 1998

Related U.S. Application Data

[63] Continuation of application No. PCT/EP97/00549, Feb. 7, 1997.

[30] Foreign Application Priority Data

Feb. 26, 1996 [DE] Germany ............................ 196 07 123

[51] Int. Cl.[7] ...................................................... A61B 17/14
[52] U.S. Cl. ............................................................... 606/180
[58] Field of Search ..................... 606/80, 180; 173/217, 173/163, 221; 310/50; 74/371, 369, 625; 408/9

[56] References Cited

U.S. PATENT DOCUMENTS

| | | | |
|---|---|---|---|
| 3,120,845 | 2/1964 | Horner | 606/180 |
| 3,734,207 | 5/1973 | Fishbein | 173/163 |
| 4,091,880 | 5/1978 | Troutner et al. | . |
| 4,493,223 | 1/1985 | Kishi et al. | 74/371 |

FOREIGN PATENT DOCUMENTS

| | | | |
|---|---|---|---|
| 0261260 | 9/1986 | European Pat. Off. | 606/180 |
| 0238204 | 2/1987 | European Pat. Off. | 606/180 |
| 0 238 204 | 9/1987 | European Pat. Off. | . |
| 0275392 | 11/1987 | European Pat. Off. | 606/180 |
| 0 261 260 | 3/1988 | European Pat. Off. | . |
| 0 275 392 | 7/1988 | European Pat. Off. | . |
| 33 17 398 | 11/1984 | Germany | . |
| 3700487 | 1/1987 | Germany | 606/180 |
| 37 00 487 | 7/1988 | Germany | . |

*Primary Examiner*—Michael Buiz
*Assistant Examiner*—Tan-Uyen T. Ho
*Attorney, Agent, or Firm*—Barry R. Lipsitz; Douglas M. McAllister

[57] ABSTRACT

In a drill for surgical purposes comprising a housing with an electric motor and a drilling mechanism driven by this electric motor arranged therein, and a handle forming part of the housing and having control grips arranged thereon for controlling the speed and reversing the direction of the electric motor, and serving to accommodate a battery and the electric control member of the electric motor, to enable sterilization without causing any damage, on the one hand, and high-power operation, on the other hand, it is proposed that a power pack comprising the battery, the electric control member, switches for speed control and reversal of direction actuatable by the control grips, and electric terminals for the electric motor arranged in the housing be insertable into the handle. The present disclosure relates to the subject matter disclosed in International Application PCT/EP97/00549 of Feb. 7, 1997, the entire specification of which is incorporated herein by reference.

12 Claims, 3 Drawing Sheets

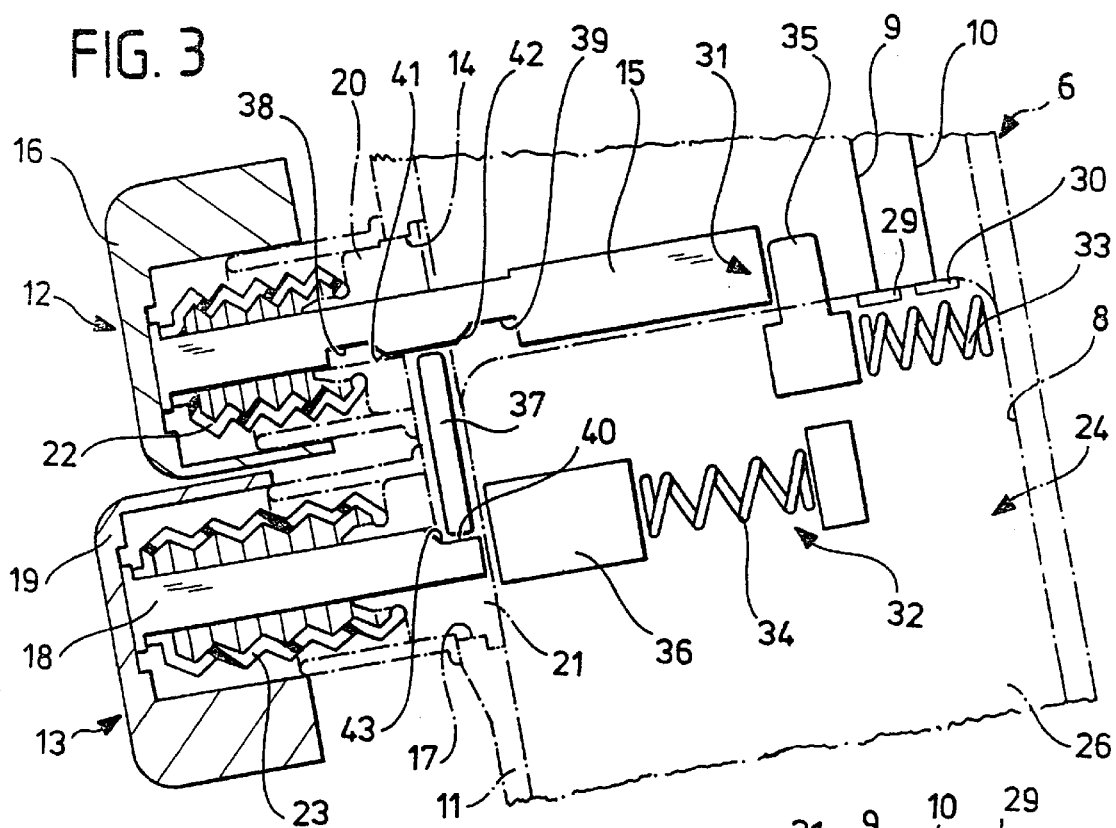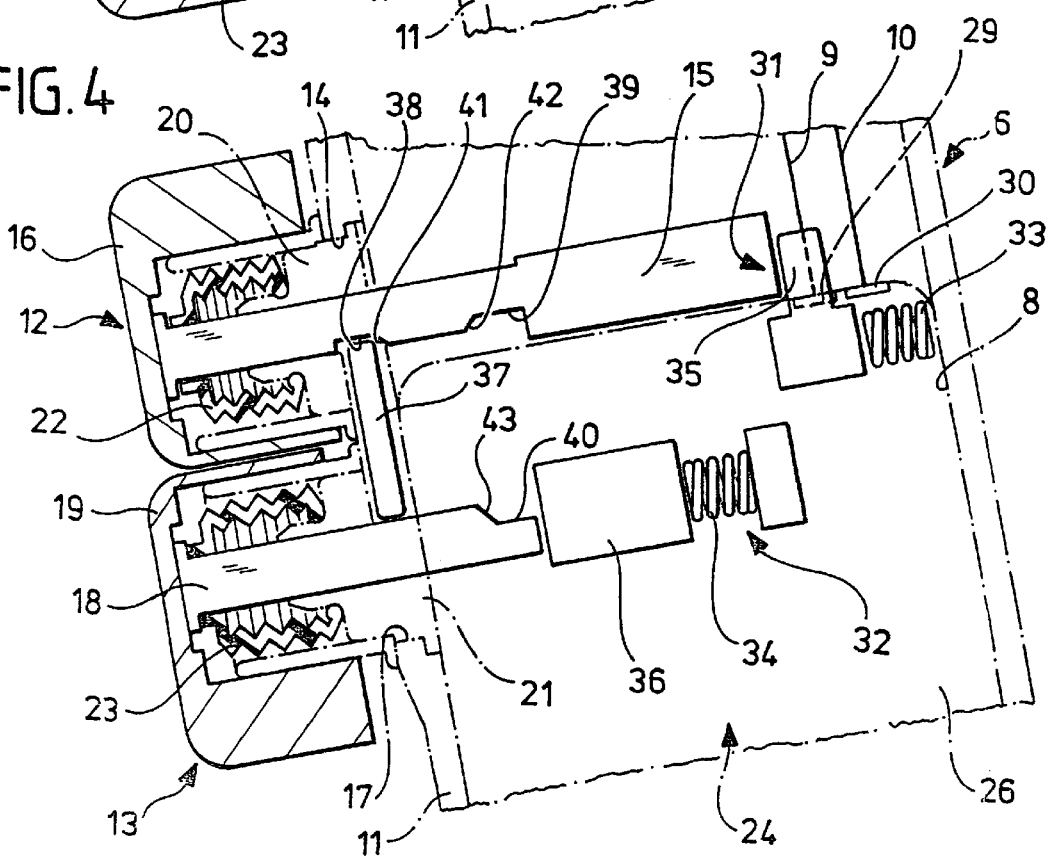

DRILL FOR SURGICAL PURPOSES

This application is a continuation of International PCT application No. PCT/EP97/00549 filed on Feb. 7, 1997.

The invention relates to a drill for surgical purposes comprising a housing with an electric motor and a drilling mechanism driven by this electric motor arranged therein, and a handle forming part of the housing and having control grips arranged thereon for controlling the speed and reversing the direction of the electric motor, and serving to accommodate a battery and the electric control means of the electric motor.

In the case of surgical hand drills, it is necessary to sterilize these appliances for each use. Sterilization is usually carried out by steam treatment at increased temperature, and this sterilizing operation may cause damage to individual components of such a drill. This applies, in particular, to electric parts.

A surgical drill is known wherein a complete drive unit is arranged in a removable handle. The drive unit consists of battery, electric control means and electric motor and is removable together with the handle from the housing (DE 33 17 398 A1). With this previously known hand drill, a mechanical coupling must be established in a complicated way between the electric motor in the handle, on the one hand, and the drive mechanism in the housing of the drill, on the other hand. It is also disadvantageous in the known hand drill that the dimensions of the electric motor are limited as there is little space for accommodating the electric motor in the handle for ergonomic reasons.

Therefore, in this way it is only possible to construct relatively weak hand drills which can be used, for example, for inserting a drill wire.

Starting from this prior art, the object of the invention is to so design a drill of the generic kind that, on the one hand, powerful drive motors can be used, and, on the other hand, it can be ensured that the sensitive parts of the hand drill will not be damaged by the sterilizing operation.

This object is accomplished in a drill of the kind described at the outset, in accordance with the invention, in that a power pack comprising the battery, the electric control means, switches for speed control and reversal of direction actuatable by the control grips and electric terminals for the electric motor arranged in the housing is insertable into the handle.

Therefore, in this drill use is made of a power pack which, in principle, is constructed to a considerable extent like a conventional battery and which can also be inserted in a similar way into the handle. However, in addition to the actual battery, this power pack also includes the electric control means and switches for speed control and reversal of direction which are actuatable by the control grips on the handle. This power pack is connected to the rest of the drill solely by electric terminals, i.e., in a way similar to an insertable battery, but a control current for the electric motor which is configured by the electric control means in accordance with the respective position of the switches for speed control and reversal of direction is delivered via the electric terminals.

Therefore, depending on the operating conditions, the power pack delivers different currents and, in this way, causes the electric motor which remains in the housing itself to selectively rotate in one direction or the other and at the respectively desired speed.

In this construction, the power pack can be designed as a completely closed off housing as is known per se from batteries. All of the other parts remain on the drill and can be sterilized with it. This applies, in particular, to the entire handle including the control grips for actuating the switches.

When assembling the drill, this power pack is inserted into the handle via a so-called sterile funnel, and the handle is then closed so the hand drill is outwardly completely sterile. Only the interior of the handle constitutes an unsterile area. However, this is in no way disturbing as the interior of the handle is completely closable, and, in particular, no opening to the rest of the hand drill is required as only electric connections are to be provided in this area.

It is particularly expedient for the power pack to comprise a lower chamber for the battery and an upper chamber for the electric control means. This results in particularly short connection paths for the electric lines as the electric connection to the housing and hence to the electric motor can be arranged on the upper side of the power pack.

It is also expedient for the switches for speed control and reversal of direction to be arranged in the upper chamber, i.e., the switches are then directly combined with the electric control means.

Insertability of the power pack is particularly simple when the power pack is pushable into the handle through the opened underside thereof.

Provision is made in a preferred embodiment of the invention for the power pack to comprise actuating elements for actuating the switches, with the control grips resting against the actuating elements when the power pack is inserted and moving these actuating elements by their own movement. Thus, a mechanical movement of the control grips is thereby transmitted onto the actuating elements on the power pack which actuate the switches arranged in the interior of the power pack.

The actuating elements are preferably movable into an initial position by spring loading. The actuating elements can then be displaced by the control grips against the loading of these springs. This, in turn, results in the spring-loaded actuating elements driving the control grips back into the initial position.

Provision may be made in a preferred embodiment for an actuating element on the upper side of the power pack to project from the latter and to be mounted on the power pack for displacement transversely to the longitudinal direction of the handle.

Further provision may be made for an actuating element to be mounted in the interior of the power pack for displacement transversely to the longitudinal direction of the handle, and for an opening through which a control grip and the actuating element rest against one another to be provided in the front side of the power pack.

This assembly may be optionally sealed off, for example, by a flexible diaphragm.

It is particularly expedient for the control grips to comprise a mutual locking mechanism which prevents simultaneous actuation of the two control grips. This ensures that during normal operation a reversal of direction is impossible, and that, in addition, the motor cannot be set in operation when the choice of direction has not yet been completed.

Provision is made in a preferred embodiment for the control grips to pass through openings in the front wall of the handle into the interior thereof and for the openings to be closed by flexible diaphragms embracing the control grips. In particular, the diaphragms may have the shape of a bellows. The interior of the handle can thereby be closed off completely from the exterior although movable parts pass through openings into the interior. This is of major importance in making the hand drill sterile.

Figure 2:
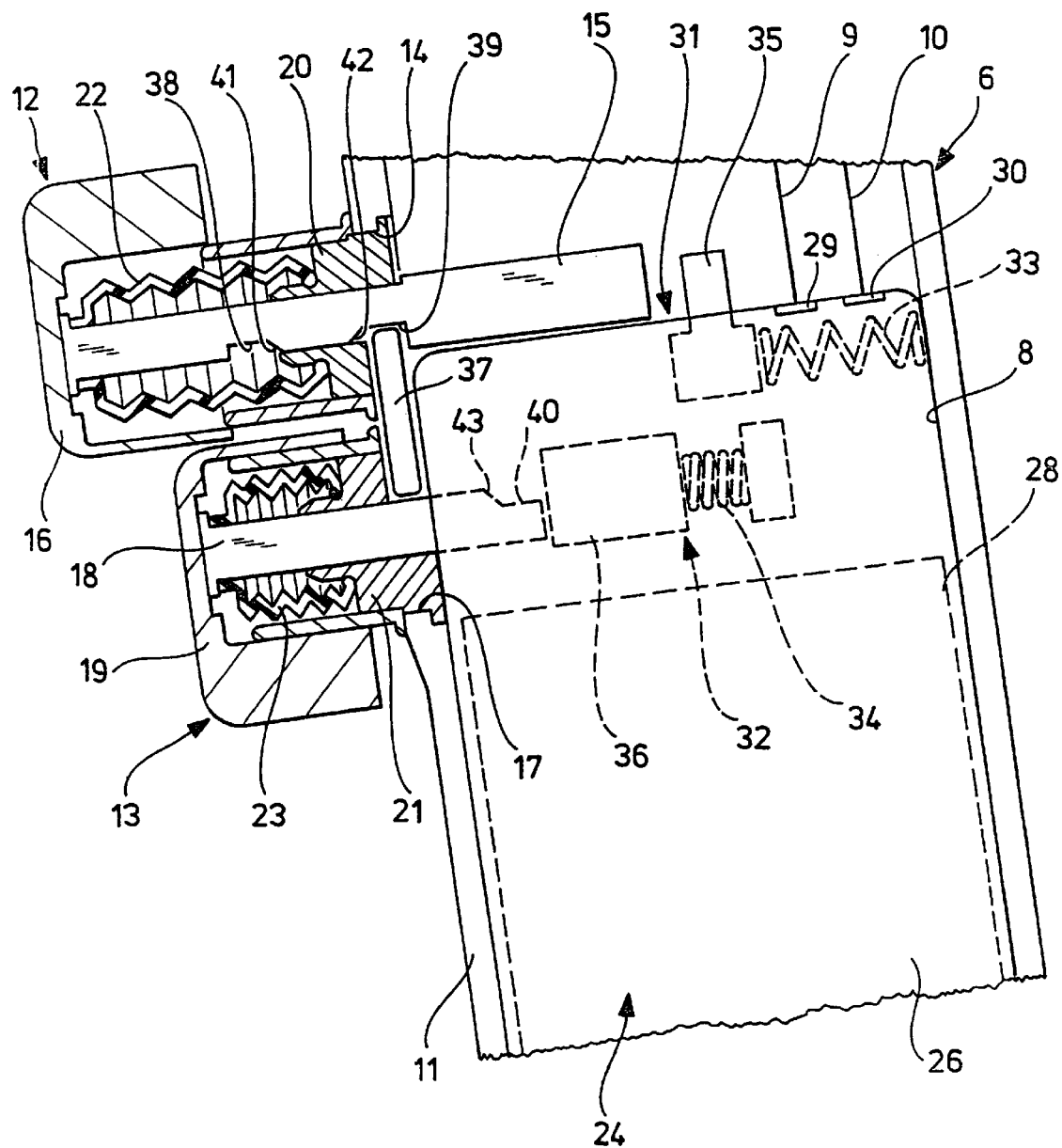

The following description of preferred embodiments of the invention serves in conjunction with the drawings for further explanation. The drawings show:

FIG. 1 a schematic side view of a hand drill with a handle and a power pack inserted therein;

FIG. 2 a longitudinal sectional view of the handle with inserted power pack in the area of the control grips with the directional switch in one position and the operating switch in working position;

FIG. 3 a view similar to FIG. 2 with the directional switch during the reversal and the operating switch in off position; and FIG. 4 a view similar to FIG. 2 with the directional switch in the other position and the operating switch in working position.

The drill 1 shown in the drawings comprises a housing 2 having arranged therein an electric motor 3 and a drive mechanism 4 for a drill chuck 5, which are shown only schematically in the drawings. These components may be of optional design as they are known per se to those skilled in the art.

Adjoining the lower end of the housing 2 is an elongate, block-shaped handle 6 which is closed off on its underside by a cover 7 which can be screwed or pushed onto it. The interior 8 of the handle 6 is closed off from the interior of the housing 2 by a dividing wall which is not shown in the drawings.

In this area, two electric connections 9, 10, shown only schematically in FIG. 1, pass from the interior 8 of the handle 6 into the interior of the housing 2.

Two control means, namely an upper directional switch 12 and a lower operating switch 13, are arranged one above the other in the front wall 11 of the handle 6 at the upper end thereof immediately beside the housing 2.

The directional switch 12 has mounted for longitudinal displacement in an opening 14 a plunger 15 which passes through the opening 14 and through the front wall 11 into the interior 8 and is connected at its free end to a gripping hood 16. In like manner, the operating switch 13 has mounted for longitudinal displacement in an opening 17 a plunger 18 which passes through the opening 17 into the interior 8 and is connected to a gripping hood 19. Both plungers 15 and 18 are mounted in inserts 20 and 21, respectively, which are placed in the corresponding openings 14 and 17, respectively. Both plungers 15 and 18 are each surrounded by a cylindrical bellows 22 and 23, respectively, which can, for example, consist of a rubber elastic material and which is fixed, on the one hand, at the respective plunger 15, 18 and, on the other hand, at the respective insert 20 and 21, respectively, so the openings 14 and 17 are thereby sealed tight. Nevertheless, the plungers 15 and 18 are displaceable in the openings 14 and 17, respectively.

A block-shaped power pack 24 with its interior divided into a lower chamber 25 and an upper chamber 26 is inserted into the interior 8 of the handle 6. A conventional, preferably rechargeable battery 27 is arranged in the lower chamber 25. An electronic control means 28 is located in the upper chamber 26. Both the battery 27 and the electronic control means are represented only schematically and in dashed lines in the drawings.

The electronic control means 28 is connected, on the one hand, electrically to the battery 27, and, on the other hand, through the lines 9 and 10 to the electric motor 3. To this end, electric contacts 29 and 30 are provided on the upper side of the power pack 24 for establishing an electric connection with the lines 9 and 10 and upon pushing the power pack 24 into the interior 8 automatically make the electric connection with the lines 9 and 10.

Also arranged in the upper chamber 26 are a directional switch 31 and a switch 32 which switches on and off the power supply to the electric motor 3 and which also adjusts switch elements in the electronic control means 28 such that the operating voltage delivered to the electric motor 3 is varied and hence drives the electric motor 3 at different speeds. Such switch elements are known per se and will, therefore, not be explained in greater detail.

The directional switch 31 comprises an actuating element 35 which is mounted in the interior of the upper chamber 26 for displacement against the action of a spring 33 and projects upwards above the power pack 24. In this area, the plunger 15 rests against the actuating element 35 so the actuating element 35 is displaced against the action of the spring 33 when the plunger 15 is pushed into the interior 8. The actuating element 35 thereby actuates a switch, not shown in greater detail in the drawings, which reverses the direction of the electric motor, i.e., in one end position prepares the electronic control means 28 for operation of the electric motor in one direction, in the other end position for the opposite direction.

Likewise mounted in the upper chamber 26 for displacement in the direction of extension of the plunger 18 is a further actuating element 36 which is pushed via a spring 34 against the plunger 18 so the plunger 18 is displaced into the pushed-out position under the action of the spring 34. The actuating element 36 can be displaced against the action of the spring 34 by pushing in the plunger 18. When the spring 34 is relaxed the electric motor is switched off. The pushing-in against the action of the spring 34 causes such adjustment of the electronic control means 28 that as the depth to which the plunger 18 is pushed in increases, the speed of the electric motor 3 is increased.

As the plungers 15 and 18 only rest against the corresponding actuating elements 35 and 36, respectively, the power pack 24 can be removed downwardly from the handle 6 at any time and reinserted after charging of the battery. After the power pack 24 is pushed in, the drill is immediately ready for operation again.

A special locking mechanism is provided for preventing reversal of the direction during operation of the electric motor and for excluding the possibility of setting the electric motor in operation when the reversal of the direction has not yet been completed. This comprises a pin 37 mounted transversely to the direction of displacement of the plungers 15 and 18 for displacement between these and having a length which is slightly greater than the distance between the two plungers 15 and 18. The upper plunger 15 has two recesses 38 and 39 arranged in spaced relation to one another and facing the other plunger 18. The plunger 18 has a single recess 40 facing the plunger 15.

All recesses 38, 39 and 40 are provided on one side thereof with a slide surface 41, 42 and 43, respectively, by means of which the pin 37 engaging the corresponding recess can be lifted out of the corresponding recess upon displacement of the corresponding plunger. However, this lifting out is only possible when a recess in the respective other plunger is located opposite. If this is not the case, the pin strikes the corresponding plunger and prevents the pin from being lifted out of the recess and hence also displacement of the plunger in whose recess the pin engages.

In the illustration in FIG. 1, both plungers 15 and 18 are in the pushed-out position under the influence of the springs 33 and 34, and in this position the recess 40 of the lower plunger 18 is in alignment with the pin 37 as is the recess 39 of the plunger 15 that is located closer to the handle 6. Starting from this position of rest, the operator can selectively actuate the directional switch 12 or the operating switch 13. The pin 37 is thereby pushed into the recess of the respective other, then unactuated plunger.

If both plungers are simultaneously actuated, this is not possible because the pin 37 can then not enter one of the recesses. Simultaneous actuation is thus blocked.

In FIG. 2, the operating position is shown in which the electric motor runs in one direction. The directional switch 12 is in the pushed-out position, and its recess 39 is in alignment with the pin 37. The operating switch 13 can be moved into an optional position, i.e., in this position drilling can be carried out at optional speed in one direction.

Simultaneous actuation of the directional switch 12 is impossible because the pin 37 cannot be lifted out of the recess 39.

This is only possible again when the operating switch 13 is in its pushed-out off position (FIG. 3), the pin 37 can then engage the recess 40 of the lower plunger 18 and thereby releases the upper plunger 15, the directional switch 12 can be actuated. However, simultaneous actuation of the operating switch 13 is not possible before the directional switch 12 has been pushed in fully, i.e., before the pin 37 can engage the recess 38 of the directional switch 12. Thus, the electric motor can only be set in operation when the reversal of the direction is completed.

Finally, FIG. 4 shows operation in this mode of operation with the direction reversed. The pin now engages the recess 38 of the upper plunger 15 and thereby releases the lower plunger 18.

By means of this relatively simple locking mechanism it is ensured that always only one of the two switches 12 or 13 can be actuated.

What is claimed is:

1. A drill for surgical purposes comprising:

a housing with an electric motor;

a drilling mechanism driven by said electric motor arranged in said housing;

a handle provided on said housing and having control grips arranged thereon to actuate switches for controlling the speed and reversing the direction of said electric motor, said handle serving to accommodate a power pack for said electric motor; wherein:

said power pack is insertable into said handle, said power pack comprising a battery, an electric control means, said switches, and electric terminals for said electric motor.

2. A drill as defined in claim 1, wherein said power pack comprises a lower chamber for said battery and an upper chamber for said electric control means.

3. A drill as defined in claim 2, wherein said switches for speed control and reversal of direction are arranged in said upper chamber.

4. A drill as defined in claim 1, wherein said power pack is insertable into said handle through an open underside thereof.

5. A drill as defined in claim 1, wherein said power pack comprises actuating elements adapted to actuate said switches, said control grips resting against said actuating elements for moving said actuating elements in response to movement of the control grips when said power pack is inserted in said handle.

6. A drill as defined in claim 5, wherein said actuating elements are moved into an initial position by spring loading.

7. A drill as defined in claim 5, wherein an actuating element on the upper side of said power pack projects from the latter and is mounted on said power pack for displacement transversely to a longitudinal direction of said handle.

8. A drill as defined in claim 5, wherein:

an actuating element is mounted in the interior of said power pack for displacement transversely to the longitudinal direction of said handle, and an opening is provided in the front side of said power pack through which a control grip and said actuating element rest against one another when said power pack is inserted in said handle.

9. A drill as defined in claim 1, wherein said control grips comprise a mutual locking mechanism which prevents simultaneous actuation of both control grips.

10. A drill as defined in claim 1, wherein:

said control grips pass through openings in a front wall of said handle into the interior thereof, and said openings are closed by flexible diaphragms embracing said control grips.

11. A drill as defined in claim 5, wherein:

said control rips pass through openings in a front wall of said handle into the interior thereof, and said openings are closed by flexible diaphragms embracing said control grips.

12. A drill as defined in claim 10, wherein said flexible diaphragms embracing said control grips have the shape of a bellows.

* * * * *